US006787323B2

(12) United States Patent
Batley et al.

(10) Patent No.: US 6,787,323 B2
(45) Date of Patent: Sep. 7, 2004

(54) VEGF RESPONSIVE CELL-BASED ASSAY FOR DETERMINING VEGF BIOACTIVITY

(75) Inventors: Brian Lee Batley, Ann Arbor, MI (US); Tawny Kay Dahring, Ann Arbor, MI (US); Sotirios K. Karathanasis, Saline, MI (US); Robert Lee Panek, Ann Arbor, MI (US); Ye Edward Tian, Canton, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/072,767

(22) Filed: Feb. 7, 2002

(65) Prior Publication Data

US 2002/0110830 A1 Aug. 15, 2002

Related U.S. Application Data

(60) Provisional application No. 60/268,202, filed on Feb. 12, 2001.

(51) Int. Cl.$^7$ .......................... G01N 33/53; C12Q 1/02; C12P 21/02; C12N 9/12
(52) U.S. Cl. ........................... 435/7.23; 435/4; 435/29; 435/69.7; 435/90.51; 435/194; 435/325
(58) Field of Search ........................... 435/29, 4, 7.23, 435/7.11, 40.51, 69.7, 194, 325

(56) References Cited

U.S. PATENT DOCUMENTS 5,981,569 A 11/1999 Gaxit et al.

FOREIGN PATENT DOCUMENTS

WO  WO 94/11499  * 5/1994

OTHER PUBLICATIONS

Wen et al., Lipocorton V may functionas a signaling protein for vascular endothelial growth factor receptor–2/Flk–1, 1999, Boichemical and Biophysical Research Communications, vol. 258, pp. 713–721.*
Murata et al., Vascular endothelial growth factor (VEGF) enhances the expression of receptors and activates mitogen–activated protein (MAP) kinase of dog retinal capillary endothelial cells, 2000, Journal of Ocular Pharamacology, vol. 16, pp. 383–391.*

Shibuya et al., Signal transduction of vascular endothelial growth factor (VEGF) receptors, Flt–1 and KDR/Flk–1, 1999, Elsevier Science, pp. 25–33.*

Hexdall et al., Stable HeLa luciferase receptor cell lines expressing GAL4 fusion transactivators, 1999, STRATE-GIES, vol. 12.*

Xu et al., In vivo signal transduction pathway reporting systems, 1997, STRATEGIES, vol. 10, pp. 1–3.*

Kroll, et al., The vascular endothelial growth factor receptor KDR activates multiple signal transduction pathways in porcine aortic endothelial cells, J. Biol. Chem. 272(51):32521–32527 (1997).

Doanes, et al., VEGF Stimulates MAPK through a Pathway That is Unique for Receptor Tyrosine Kinases, Biochem. Biophys. Res. Comm., 255:545–548 (1999).

Wedge, et al., Inhibition of VEGF Signal Transduction, Angiogenes: From the Molecular to Integrative Pharmacology, Adv. Exp. Med. Biol., 476:307–310 (2000).

Wedge, et al., ZD4190: An orally active inhibtion of vascular endothelial growth factor signaling with broad–spectrum antiumor efficacy, Cancer Res., 60(4):970–975 (2000).

Petrova Tatiana V., et al., Signaling via vascular endothelial growth factor receptors, Experimental Cell Research, 253(1):117–130 (1999) (XP–002198305).

Hexdall L., et al., Stable report cell lines for signal transduction pathway readout, Proceedings of the American Asso, for Cancer Research Annual, 40:332 (1993) (XP–001071251).

Groot, et al., Accession No.: PREV200100114456, Database Biosis Online, Biosciences Information Service, Philadelphia, PA, US, 2000–12 (Dec. 2000) (Abstract) (XP–002198309).

* cited by examiner

*Primary Examiner*—Anne-Marie Falk
*Assistant Examiner*—Daniel M. Sullivan
(74) *Attorney, Agent, or Firm*—Peter C. Richardson; Seth H. Jacobs

(57) ABSTRACT

A VEGF responsive cell-based assay for determining VEGF bioactivity is disclosed. The assay utilizes established signal transduction pathways in a method for determining VEGF bioactivity in a sample.

2 Claims, 12 Drawing Sheets

VEGF RESPONSIVE CELL-BASED ASSAY FOR DETERMINING VEGF BIOACTIVITY

This application claims the benefit of priority, under 35 U.S.C. §119(e), to U.S. provisional application Ser. No. 60/268,202, filed Feb. 12, 2001.

FIELD OF THE INVENTION

The present invention generally relates to detection of vascular endothelial growth factor (VEGF) in a sample. Specifically, the present invention relates to a VEGF responsive cell-based assay for use in the measurement of the biological activity of VEGF.

BACKGROUND OF THE INVENTION

A number of biological properties have been described for VEGF, including the promotion of angiogenesis. Other properties include endothelial cell migration, endothelial cell proliferation, in vitro capillary tube formation, inhibition of endothelial cell apoptosis, and increased in vivo vascular permeability producing edema.

Because VEGF appears to have a number of significant biological properties, assays for the detection of VEGF and its properties have become increasingly important.

One in vitro bioassay which has been developed is based on the ability of human umbilical vein endothelial cells (HUVEC) to migrate in response to VEGF. This bioassay includes the steps of first virally transfecting Rat-2 cells with the consequent production of VEGF protein, and then testing the produced protein extract for the ability to stimulate HUVEC migration. While this assay can be utilized to demonstrate endothelial cell migration stimulated by VEGF protein in the conditioned media of cells, this assay includes a number of time-consuming steps, which cannot easily be automated.

Recently, it was proposed that VEGF could be a marker of cardiovascular disease risk in patients with hypertension. The measurement of a patient's VEGF and/or FLT-2 levels may be an indicator of the effectiveness of a hypertensive therapy.

Currently, with the seemingly greater importance of VEGF, it would be both advantageous and desirable to have a VEGF responsive assay that is less complex than previous assays, that can be automated, and that is also directly linked to a reporter protein tied to the VEGF receptor (VEGF-R)/FLK-1 signal transduction pathway.

SUMMARY OF THE INVENTION

The present invention provides a method for determining VEGF activity in a sample.

The present invention also relates to a secondary screen which is useful for identifying compounds that modulate VEGF receptors.

The present invention also provides a primary screening mechanism for screening compounds as inhibitors of VEGF function.

The present invention also provides a stable cell line for use in determining VEGF bioactivity and for use in screening compounds which modulate VEGF function or VEGF receptor function.

BRIEF DESCRIPTION OF THE FIGURES

Other advantages of the present invention will be readily appreciated as the same becomes better understood by reference to the following detailed description when considered in connection with the accompanying drawings wherein:

FIG. 1b is a graph illustrating a VEGF responsive assay similar to that shown in FIG. 1a wherein the concentration of VEGF utilized in the assay was increased to 50 ng/mL as opposed to 25 ng/mL in FIG. 1a;

DETAILED DESCRIPTION OF THE INVENTION

Figure 1A:
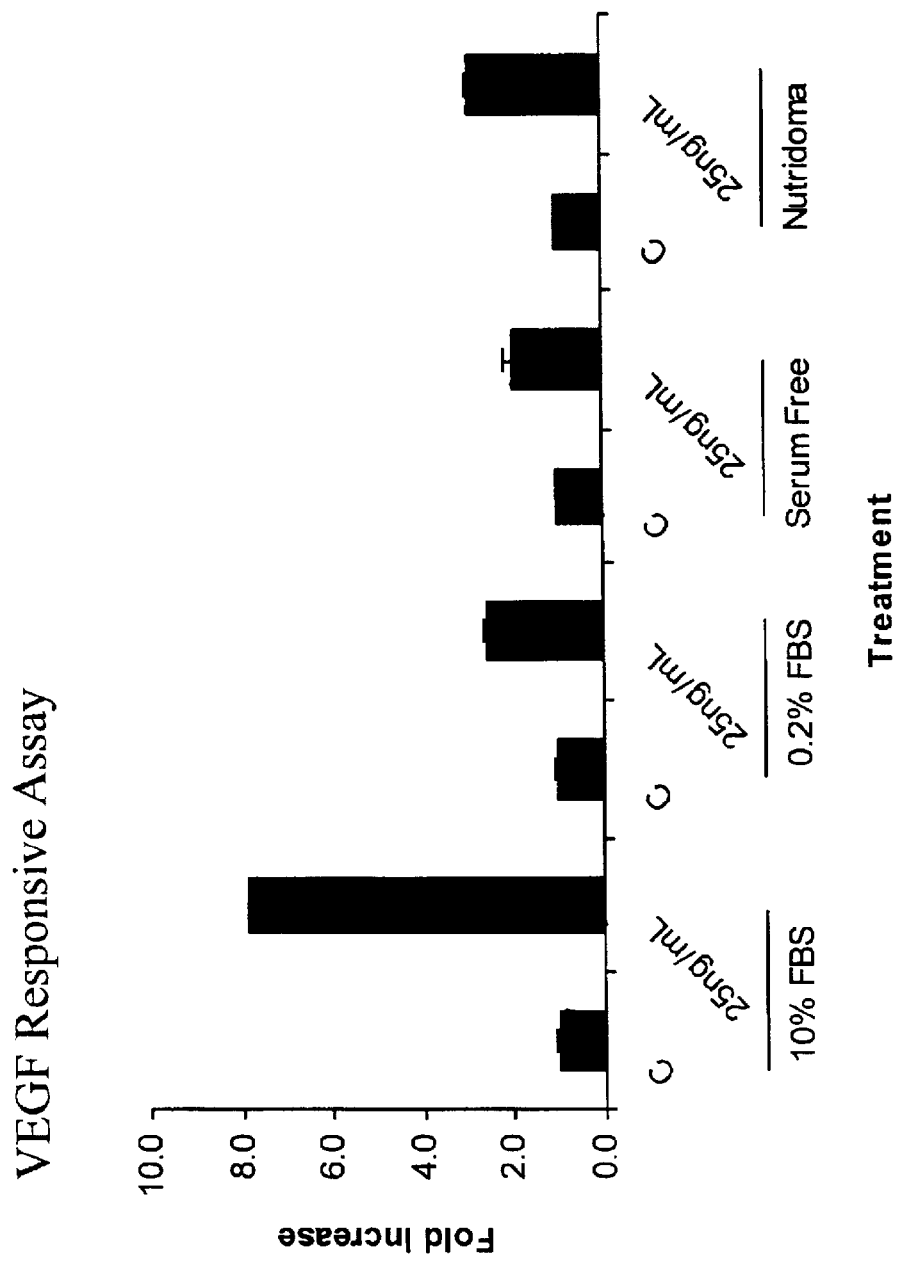
FIG. 1a is a graph illustrating a VEGF responsive assay wherein the effects of various serum preincubation conditions are shown as a function of increased luciferase expression wherein cells were seeded 24 hours prior to VEGF addition and were harvested 48 hours after VEGF addition.

The present invention provides a VEGF responsive cell-based assay and stable cell line for use therewith for determining VEGF bioactivity. The assay of the present invention allows for the measurement of the bioactivity of VEGF derived from biological samples including plasma, cell culture medium, tissue extracts from tissues or cells transfected with VEGF DNA sequences, or combinations thereof. The method of the present invention can also be adapted for use in high throughput screening and in secondary screens to identify novel small molecule modulators (inhibitors or activators) of a VEGF receptor, specifically FLK-1.

The methods of the present invention use a VEGF responsive HeLa cell line which is stably transfected with 1) a reporter vector having an expressible reporter element and a DNA binding element disposed adjacent thereto, preferably the reporter vector includes a gene encoding a detectable gene product which is disposed downstream of a basic promoter element. preferably a TATA box, which is joined to the binding element which is preferably a GAL4 binding element; 2) a CMV promoter driven vector encoding a fusion protein composed of the yeast GAL4 binding domain and the transactivation domain of the transcription factor ELK-1: and 3) a vector encoding a FLK-1 VEGF receptor. The cell lines of the present invention can be used to demonstrate upregulation of the detectable gene product (e.g. luciferase) in the presence of VEGF. That is, utilizing established signal transduction pathways, VEFG bioactivity can be assayed.

In general, utilizing known signal transduction relationships and/or pathways, a sample to be assayed for VEGF bioactivity is placed in a container containing the stable cell line as described above. If VEGF is present in the sample, VEGF activates FLK-1 expressed by the stable cell line. Activated FLK-1, which is a known VEGF receptor, then activates MAP kinase (Kroll and Waltenberger, *J. Biol. Chem.*, 1997:272:32521–32527; Doanes et. al., *Biochem. Biophys. Res. Comm.*, 1999;255:545–548). The activated MAP kinase phosphorylates the fusion trans-activation protein (GAL4 DNA binding domain [dbd] fused with ELK-1). The phosphorylated fusion protein binds to the GAL4 DNA binding site of the reporter vector activating luciferase expression. Luciferase expression can be detected utilizing techniques well-known in the art. The presence or expression of luciferase indicates VEGF activity in the sample.

EXAMPLES

The following examples further illustrate the present invention. The examples are intended merely to be illustrative of the present invention and are not to be construed as being limited.

Methods
Cell Line Production

HeLa cells stably transfected with the GAL4 luciferase reporter and a vector expressing a fusion protein composed of the GAL4 DNA binding domain and the transactivation domain of the transcription factor ELK-1 (GAL4-ELK-1-fusion) were purchased from Stratagene Inc. These cells were co-transfected with a CMV driven FLK-1 expression vector (licensed from The Ludwig Institute, Germany) and a Zeocin selection expression vector (pcDNA3.1/zeo (+), #V860-20) obtained from Invitrogen in the HeLa cells. After appropriate antibiotic selection, stable transfectants were identified that respond to VEGF by increasing luciferase expression.

Cell Culture and Luciferase Assay

The optimal transfected VEGF-receptor cell line (referred to as clone #5) was maintained in Dulbecco's Modified Eagle Medium (Life Technologies, Gaithersburg, Md.) containing 10% fetal bovine serum (FBS), Geneticin (250 μg/mL), Hygromysoin B (100 μg/mL), and Zeocin (100 μg/mL). Cells were seeded into 24-well culture plates and allowed to attach prior to the stimulation of luciferase production by the addition of $VEGF_{121}$ (298-VS-005, R&D Systems, Minneapolis, Md.) at the indicated concentrations. Luciferase activity was measured 24 to 48 hours poststimulation as outlined in the technical insert for the luciferase assay system available from Promega Corporation (E1501, Madison, Wis.). The cells were washed with PBS before being lysed in 200 μL of 1X reporter lysis buffer. The entire plate was frozen at −80° C. to increase cell lysis. Upon thawing, 50 μL of the cell extract was transferred into a 96-well plate. Luciferase assay reagent (100 μL) was auto-injected, and light production was measured using a microplate luminometer.

Example 1
Effect of Serum Preincubation Conditions on Luciferase Activity

Figure 1B:
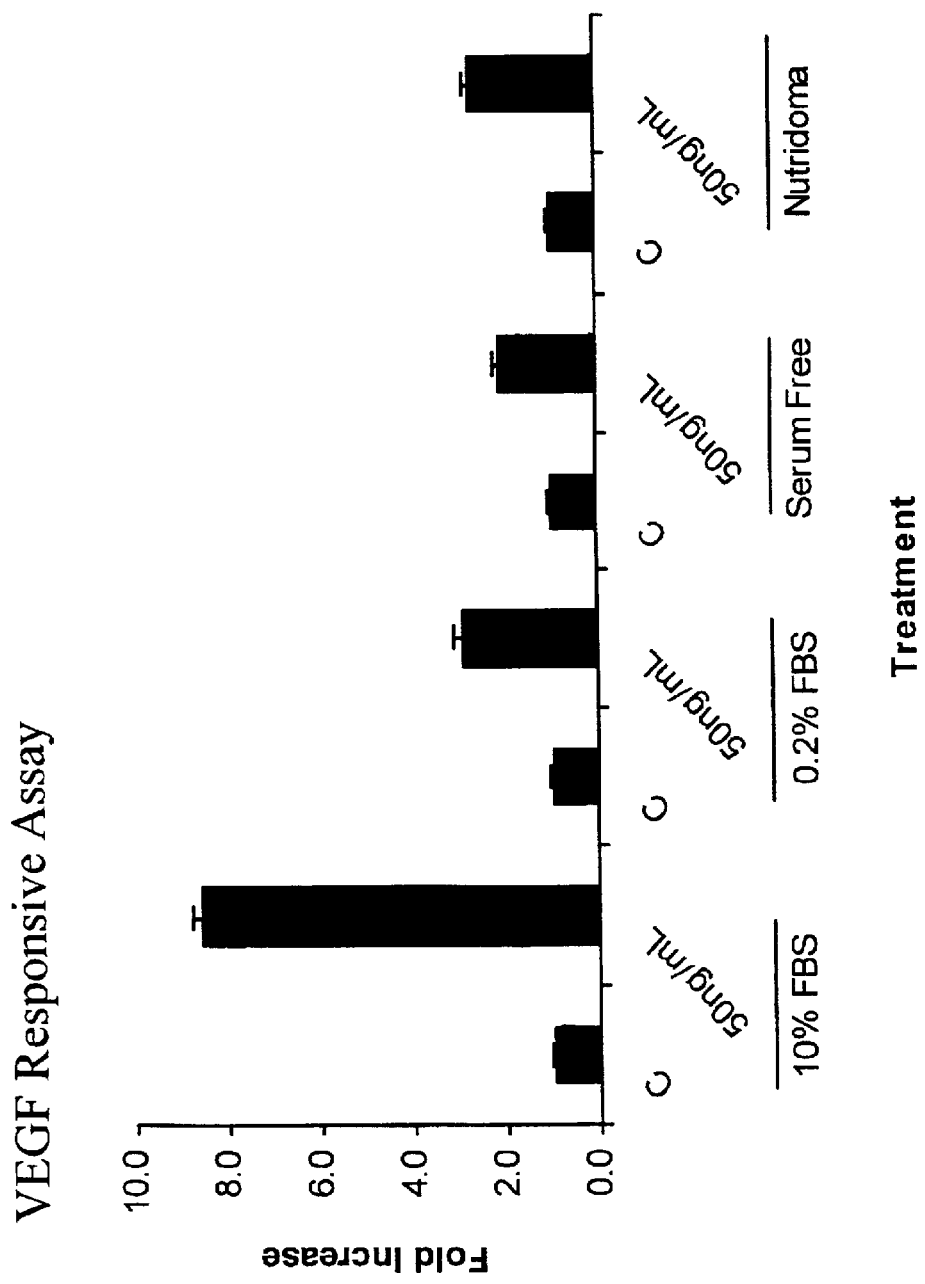

Cells were seeded into wells 24 hours prior to VEGF addition. The cells were harvested 48 hours after the addition of 25 ng/mL of VEGF. Cells were pre-incubated under various serum conditions: (1) 10% FBS, (2) 0.2% FBS, (3) serum free, and (4) nutridoma, a serum-free media supplement. The results are shown in FIG. 1a. The optimal serum pre-incubation condition was found to be preincubation in 10% FBS. An identified experiment was performed except that the concentration of VEGF added was increased to 50 ng/mL. The results are shown in FIG. 1b. The increased concentrations of VEGF was found to increase luciferase expression.

Figure 2:
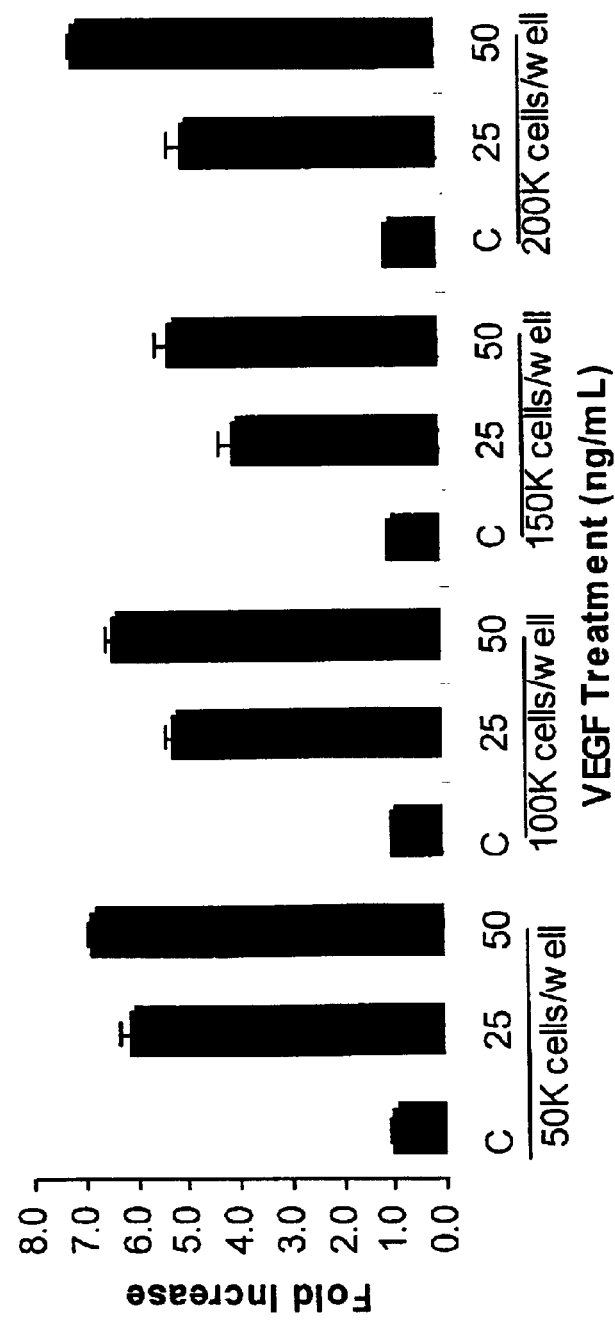
FIG. 2 is a graph illustrating the effects of cell density and $VEGF_{121}$ concentration on luciferase expression in a VEGF receptor stable transfected Hela-Luciferase HLR-ELK-1 cell line.

Example 2
Effects of Cell Density and $VEGF_{121}$ Concentration on Luciferase Expression Cells were prepared as described above. Cells were seeded into wells 24 hours prior to the addition of $VEGF_{121}$. $VEGF_{121}$ was added to the cells at concentrations of 25 and 50 ng/mL, respectively. Cells seeded into the wells were tested at densities of: 50, 100, 150, and 200 K/well. The results are shown in FIG. 2.

Example 3
Dose Response to VEGF in the Parental Cell Line (HLR-ELK-1)

Figure 3:
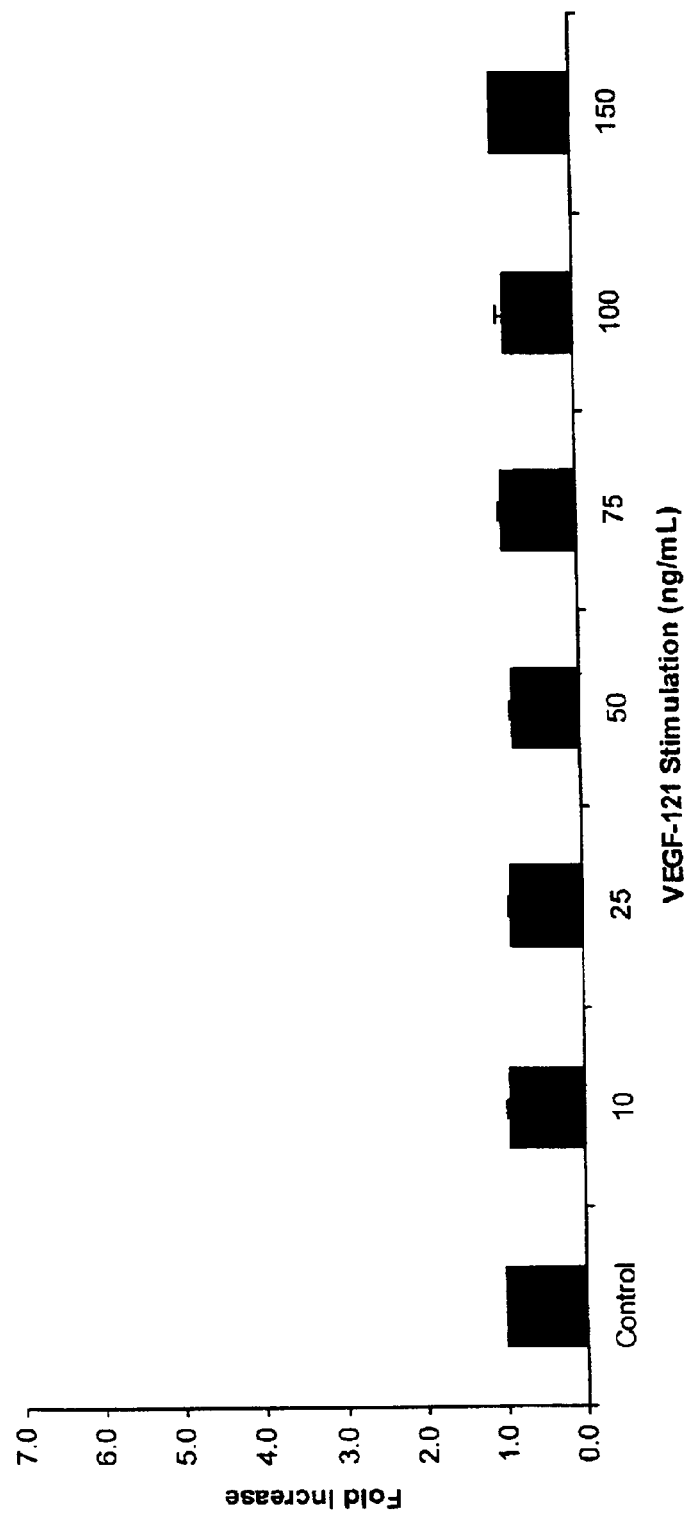
FIG. 3 is a graph illustrating VEGF stimulated production of luciferase in an HLR-ELK-1 cell line wherein the concentration of $VEGF_{121}$ was varied and the number of cells seeded in each well was kept constant at approximately 50,000.

Cells were prepared as described above. 50 K/well were seeded and kept in 10% FBS throughout the experiment. $VEGF_{121}$ was added 24 hours after seeding, and the cells were harvested and analyzed 48 hours after the addition of $VEGF_{121}$. The results are shown in FIG. 3. The results showed that the parental cell line was no more responsive to $VEGF_{121}$ stimulation than the control.

Figure 4:
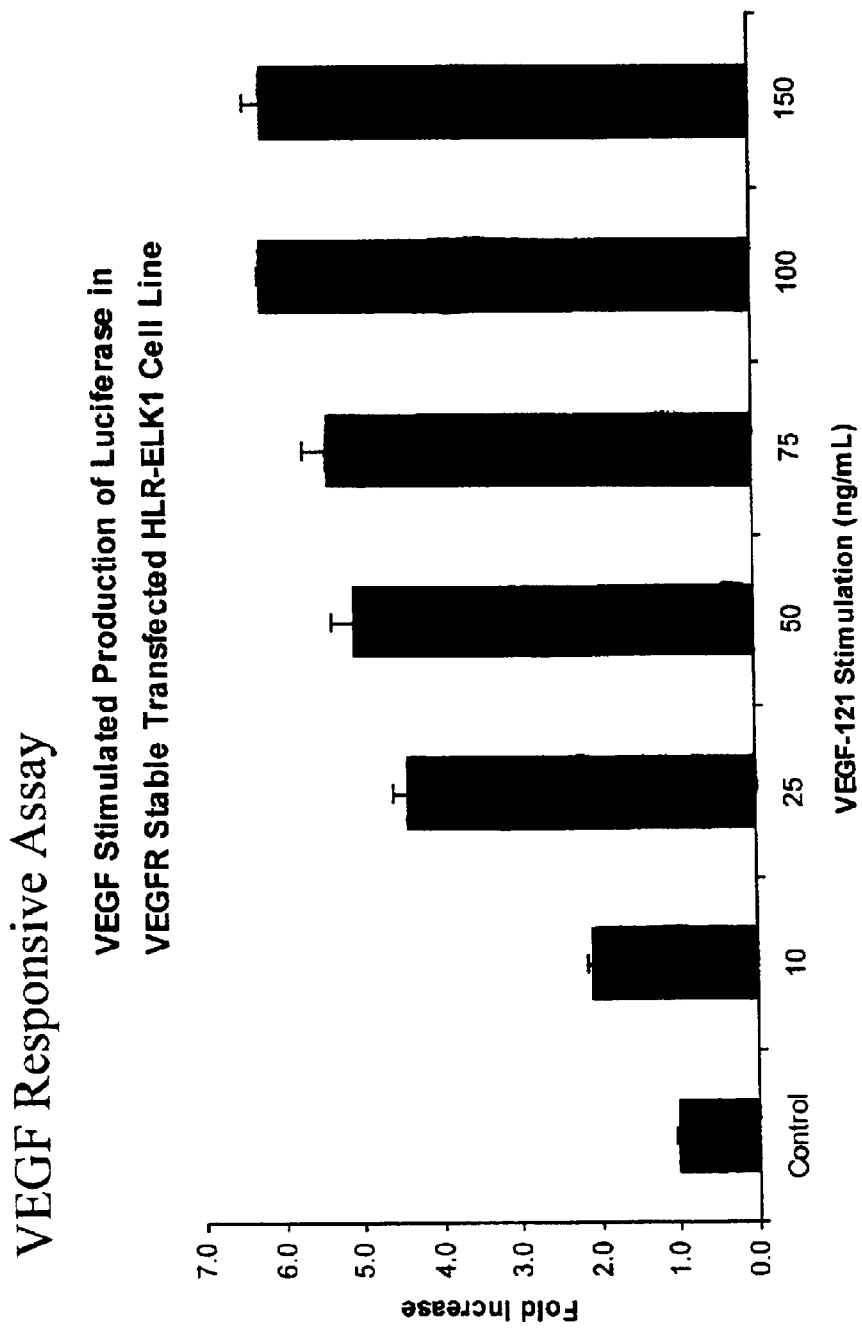
FIG. 4 is a graph illustrating VEGF stimulated production of luciferase in a VEGF receptor stable transfected HLR-ELK-1 cell line, wherein the number of cells seeded into each well was kept constant at approximately 50,000, and the concentration of $VEGF_{121}$ was varied.

Example 4
Dose Response of VEGF-Receptor Stable Transfected HLR-ELK1 Cell Line Cells were prepared as described above. Cells were transfected with the plasmid vector expressing the FLK-1 VEGF receptor were seeded at 50 K/well and maintained in 10% FBS throughout the experiment. $VEGF_{121}$ was added 24 hours after seeding, and the cells were harvested 48 hours after the addition of $VEGF_{121}$. The concentration of $VEGF_{121}$ was tested at 10, 25, 50, 75, 100, and 150 ng/mL. Maximum increase in luciferase expression was found at a $VEGF_{121}$ concentration of 100 ng/mL as shown in FIG. 4.

Example 5
Dose Responsive Specificity of the VEGF-Receptor Cell Line

To demonstrate the dose responsive specificity of the VEGF-receptor cell line, cells were prepared as described above. The transfected cells were incubated with $VEGF_{121}$, the adenovirus NULL vector (AdCLX), antihuman $VEGF_{121}$ antibodies (AF-293-NA [polyclonal], MAB293 [monoclonal], R&D Systems), a VEGF receptor-specific tyrosine kinase inhibitor (ZD4190, Zeneca [Wedge S. R., Ogilvie D. J. Inhibition of VEGF signal transduction: Identification of ZD4190. *Adv. Exp. Med. Biol.*, 2000;476 (Angiogenesis: From the Molecular to Integrative Pharmacology):307–310; and Wedge S. R., Ogilvie D., Dukes M., Kendrew J., Curwen J. O., Hennequin L. F., Thomas A. P., et. al., ZD4190: An orally active inhibitor of vascular endothelial growth factor signaling with broad-spectrum antitumor efficacy. *Cancer Res.*, 2000;60(4):970–975]), media from ADVEGF$_{121}$ transfected rat 2 cells at various concentrations, or the VEGF-receptor cell line was directly infected with an adenovirus containing VEGF$_{121}$ (Ad$_{GV}$121.10, CI-1023, GenVec, Inc., Rockville, Md.) at various concentrations.

Figure 5:
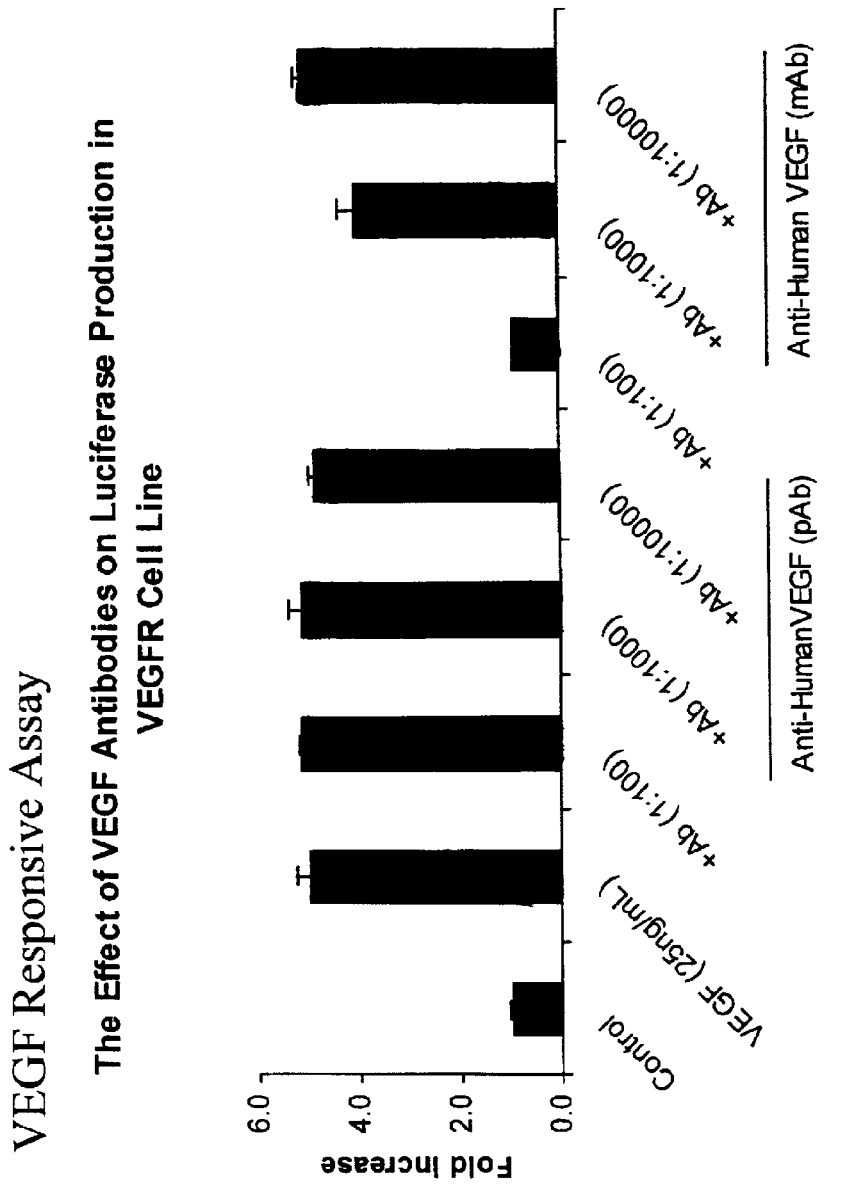
FIG. 5 is a graph illustrating the effect of VEGF antibodies on luciferase production in a VEGF receptor cell line.

Cells were seeded at 50 K/well 24 hours prior to the addition of VEGF/anti-VEGF and were collected 48 hours later. Referring to FIG. 5, the results for the antihuman VEGF antibodies are shown. The polyclonal antibodies did not significantly affect luciferase expression. The monoclonal antibodies at the 1:100 and 1:1000 dilutions affected the luciferase expression.

Figure 9:
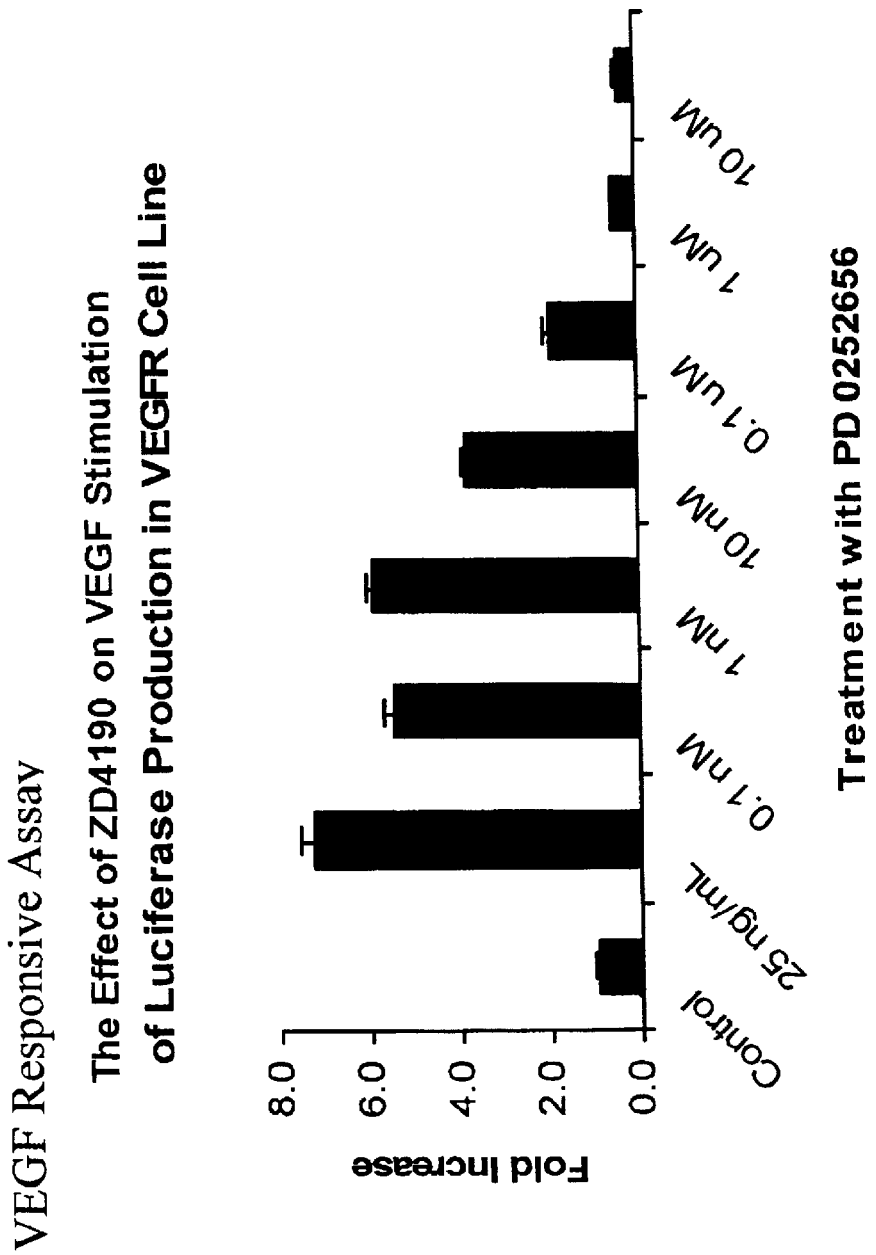
FIG. 9 is a graph illustrating the effect of compound ZD4190 (a known VEGF-receptor tyrosine kinase inhibitor) on VEGF stimulation of luciferase production in a VEGF-receptor cell line.

FIG. 9 shows the effects of the known VEGF receptor tyrosine kinase inhibitor (ZD4190) on luciferase expression. The VEGF receptor tyrosine kinase inhibitor affected luciferase expression in a dose-response manner.

Figure 10:
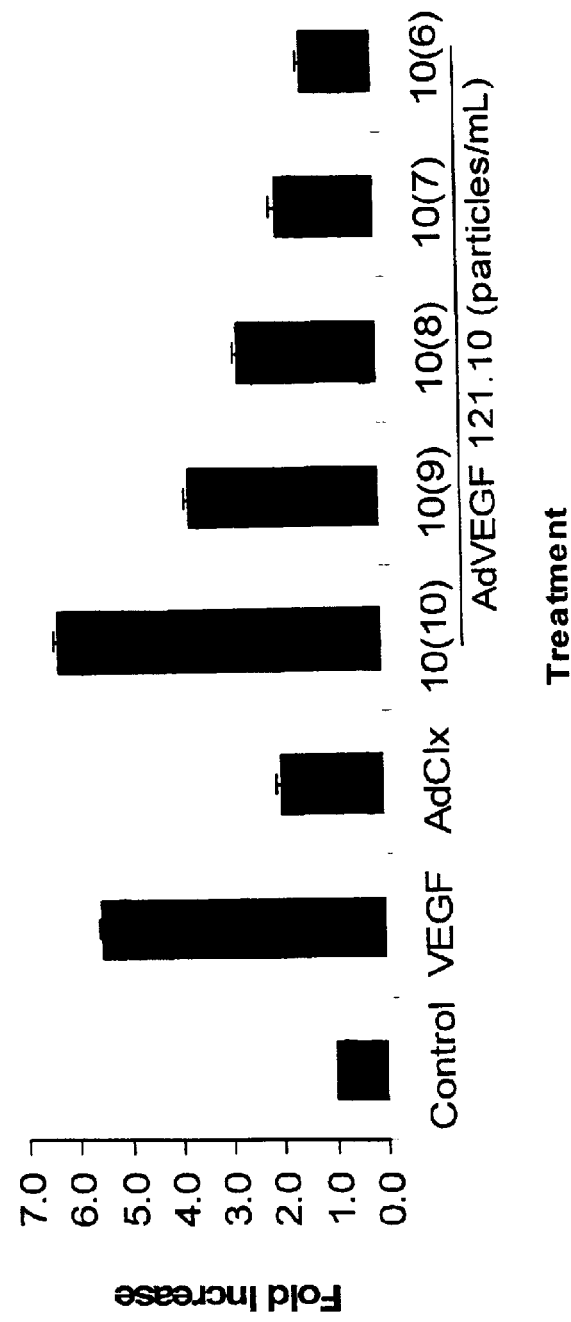
FIG. 10 is a graph illustrating luciferase production after transfection of a VEGF-receptor cell line with $AdVEGF_{121}$.
Figure 11:
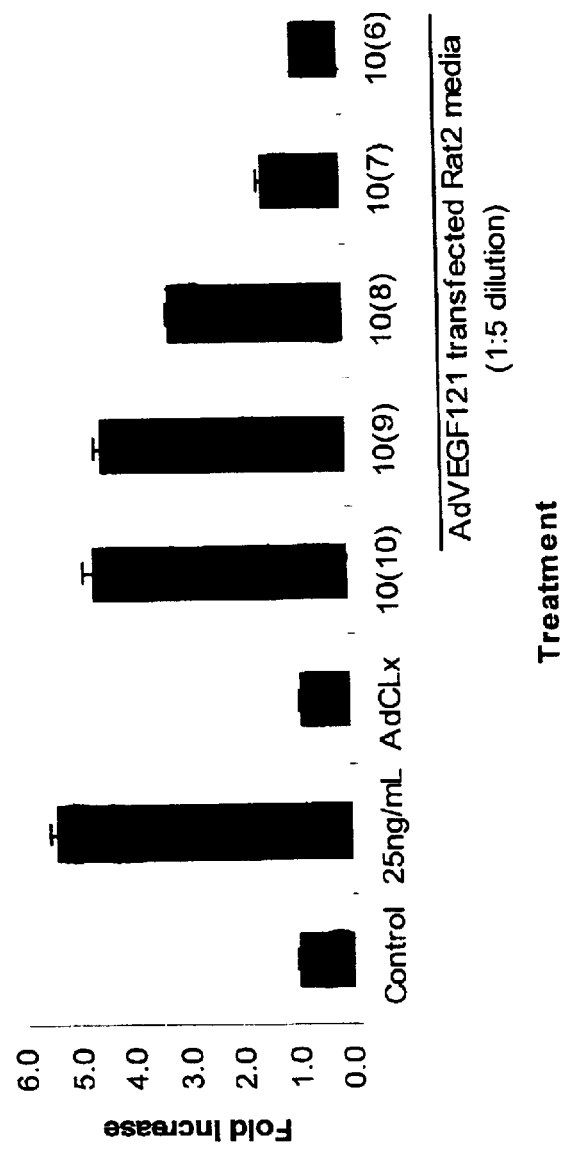
FIG. 11 is a graph illustrating VEGF stimulated luciferase production using media from $AdVEGF_{121}$ transfected Rat-2 cells.

FIG. 10 shows the effects of Ad VEGF$_{121}$ obtained from using a media from AdVEGF$_{121}$ transfected rat 2 cells. The addition of AdVEGF$_{121}$ to the VEGF-receptor cell line affected luciferase expression in a dose response manner both from the AdVFGF$_{121}$ itself and from the media from AdVEGF$_{121}$ transfected rat 2 cells.

Figure 6:
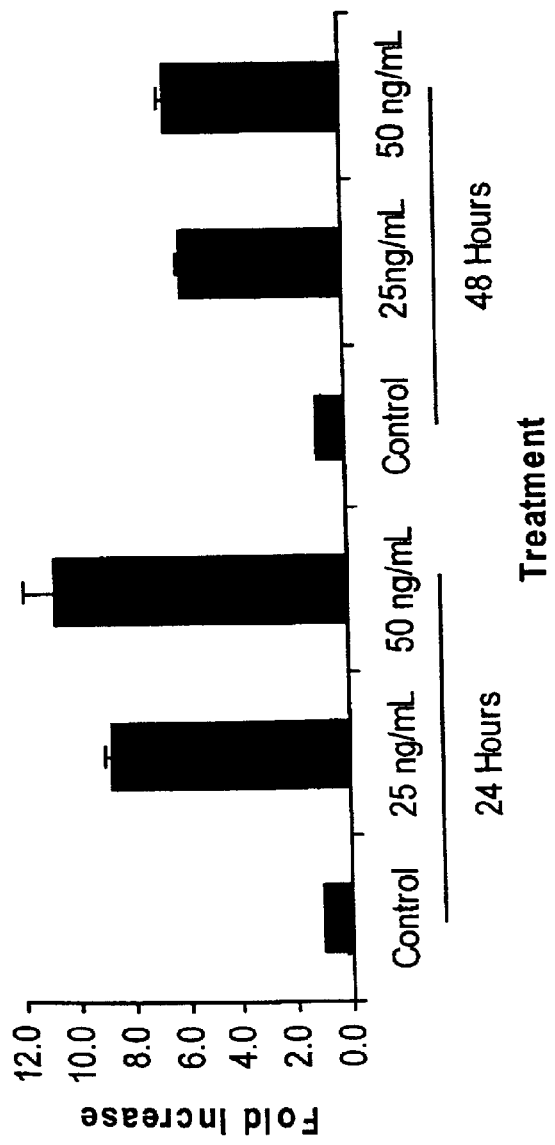
FIG. 6 is a graph illustrating luciferase production in a VEGF-receptor (VEGFR) cell line wherein incubation time was compared for 24 and 48 hours.

Example 6
Luciferase Production in VEGF-Receptor Cell Line at 24 and 48 Hours After the Addition of VEGF Cells were prepared as described above. VEGF$_{121}$ was added to cells (50 K well) 24 hours after seeding. VEGF$_{121}$ was added to the cells at concentrations of either 25 or 50 ng/mL. Luciferase expression was measured 24 hours after the addition of VEGF$_{121}$ and 48 hours after the addition of VEGF$_{121}$. The results are shown in FIG. 6. Maximum luciferase expression was found in the cells treated with 50 ng/mL of VEGF$_{121}$ at 24 hours post-VEGF$_{121}$ introduction.

Example 7
Determination of Optimal VEGF Concentration

Figure 7:
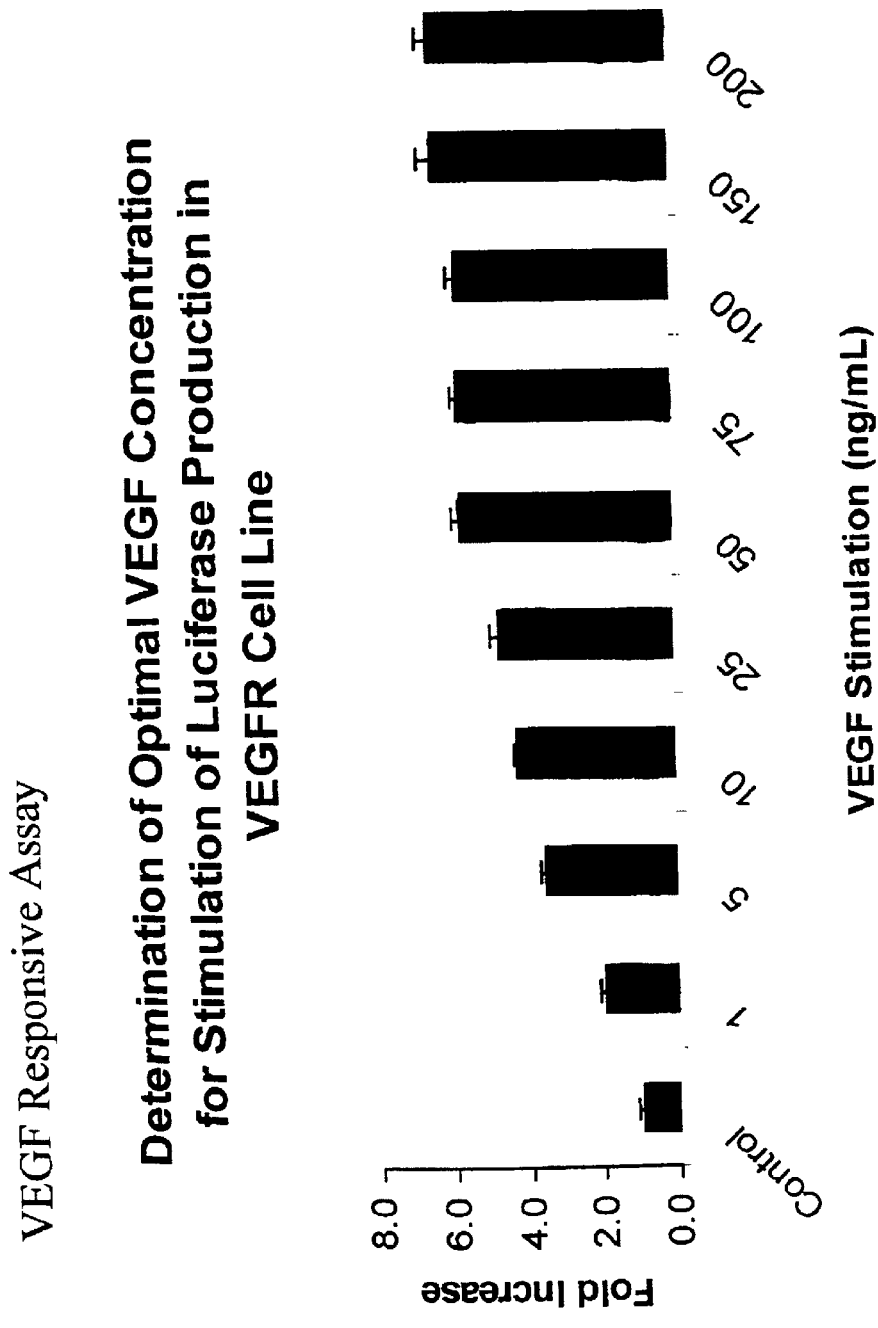
FIG. 7 is a graph illustrating the optimal VEGF concentration for stimulation of luciferase production in a VEGF-receptor cell line.

VEGF-receptor cells were seeded at 50 K/well and incubated in 10% FBS throughout the experiment. VEGF$_{121}$ was added to the cells 24 hours after seeding, and the cells were harvested 18 hours later. The VEGF$_{121}$ was applied to the cells at the following concentrations: 1, 5, 10, and 200 ng/mL. The results are shown in FIG. 7. The optimal VEGF$_{121}$ concentration ranges from approximately 50 ng/mL to approximately 200 ng/mL.

Example 8
Optimal Incubation Time for VEGF-Induced Luciferase Production

Figure 8:
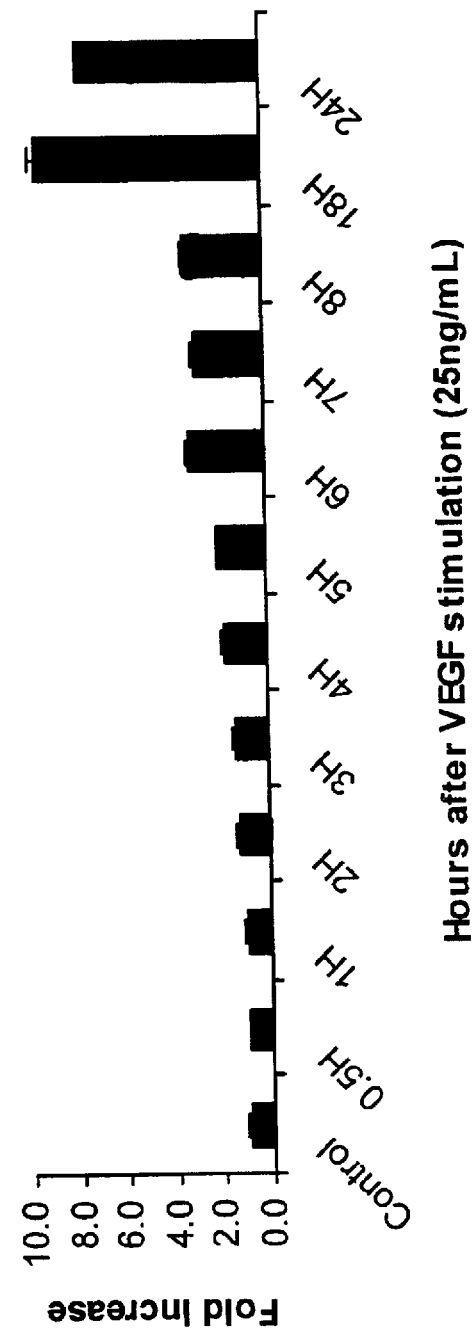
FIG. 8 is a graph illustrating the optimal time for VEGF induced luciferase production in a VEGF-receptor cell line.

Cells were prepared as described above VEGF-receptor cells were seeded at 50 K/well and incubated for 24 hours in 10% FBS prior to the addition of VEGF$_{121}$. Cells were harvested at 0.5, 1, 2, 3, 4, 5, 6, 7, 8, 18, and 24 hours, after VEGF$_{121}$ (25 ng/mL) addition. FIG. 8 shows the results of this experiment. Approximately 18 hours of expression time was found to yield maximum luciferase expression (production).

All publications mentioned in the specification are herein incorporated by reference to the same extent as if each independent publication was specifically and individually indicated to be incorporated by reference.

While the invention has been described in connection with specific embodiments thereof, it will be understood that it is capable of further modifications. The application is intended to cover any variations, uses, or adaptations following, in general, the principles of the invention and including such departures from the present disclosure within known or customary practice within the art to which the invention pertains and may be applied to the essential features herein before set forth.

What is claimed is:

1. A method for determining vascular endothelial growth factor (VEGF) activity in a sample, said method comprising the steps of:

a) contacting a sample to be assayed for VEGF activity with a stable HeLa cell line wherein the stable HeLa cell line comprises:

1) a reporter vector having; an expressible reporter element and a DNA binding site disposed adjacent thereto and, 2) a chimeric transactivator vector comprising a gene encoding a phosphorylatable protein that can be phosphorylated by MAPK and a DNA binding domain which specifically binds to the DNA binding site, and 3) an expression vector encoding a gene for a VEGF receptor; and b) detecting expression of the reporter element, wherein expression of the reporter element indicates VEGF activity wherein the sample comprises cells, tissue, tissue extracts or combinations thereof.

2. A method for determining vascular endothelial growth factor (VEGF) activity in a sample, said method comprising the steps of:

a) contacting a sample to be assayed for VEGF activity with a stable HeLa cell line wherein the stable HeLa cell line comprises:

1) a reporter vector having; an expressible reporter element and a DNA binding site disposed adjacent thereto and, 2) a chimeric transactivator vector comprising a gene encoding a phosphorylatable protein that can be phosphorylated by MAPK and a DNA binding domain which specifically binds to the DNA binding site, and 3) an expression vector encoding a gene for a VEGF receptor; and b) detecting expression of the reporter element, wherein expression of the reporter element indicates VEGF activity, and wherein the contacting step comprises incubating the sample with the stable HeLa cell line for a period of time ranging from approximately 10 hours to approximately 20 hours.

\* \* \* \* \*